United States Patent [19]

Buysch et al.

[11] Patent Number: 4,608,207
[45] Date of Patent: Aug. 26, 1986

[54] DIALKYL 2-ALKYLCARBONATOETHANEPHOSPHONATES

[75] Inventors: Hans-Josef Buysch; Peter Mues, both of Krefeld, Fed. Rep. of Germany

[73] Assignee: Bayer Aktiengesellschaft, Leverkusen, Fed. Rep. of Germany

[21] Appl. No.: 607,354

[22] Filed: May 4, 1984

[30] Foreign Application Priority Data

May 7, 1983 [DE] Fed. Rep. of Germany ....... 3316888

[51] Int. Cl.$^4$ ................................................ C07F 9/40
[52] U.S. Cl. .................................. 558/179; 558/217; 558/142
[58] Field of Search ......................................... 260/952

[56] References Cited

U.S. PATENT DOCUMENTS

| | | | |
|---|---|---|---|
| 4,182,726 | 1/1980 | Illuminati et al. | 260/463 |
| 4,387,095 | 6/1983 | Saito et al. | 260/952 |
| 4,435,331 | 3/1984 | Licciardello et al. | 260/463 |
| 4,447,365 | 5/1984 | Boden et al. | 260/463 |

FOREIGN PATENT DOCUMENTS 0065741 12/1982 European Pat. Off. .
1499530 2/1978 United Kingdom .

OTHER PUBLICATIONS

Soviet Inventions Illustrated, Section Ch: Chemical, Woche D42, 25, Nov. 1981, Derwent Publications Ltd., Agricultural Chemistry, Seite 1, No. 77135D142, London, GB; & SU-A-681 830 (Melnikov N.N.) 23.05.1981 *Zusammenfassung*.

Primary Examiner—Anton H. Sutto
Attorney, Agent, or Firm—Sprung, Horn, Kramer & Woods

[57] ABSTRACT

Dialkyl vinylphosphonates are prepared by heating the new dialkyl 2-alkylcarbonatoethanephosphonates in the presence of catalysts. Also disclosed is a process for making the new dialkyl 2-alkylcarbonatoethanephosphonate by transesterification of a dialkyl 2-carboxyethanephosphonate with a dialkyl carbonate in the presence of a transesterification catalyst.

1 Claim, No Drawings

DIALKYL 2-ALKYLCARBONATOETHANEPHOSPHONATES

The invention relates to new dialkyl 2-alkylcarbonatoethanephosphonates and their use in preparing dialkyl vinylphosphonates.

It is known to prepare dialkyl vinylphosphonates from 2-bromoethanephosphonic or 1,1- or 1,2-dichloroethanephosphonic acid esters (cf. J. Appl. Chem. 11, 352 (1961); Z. obsc. Chim. 29, 3947 (1959), C.A. 54, 20844 (1960)). The preparation via 2-bromoethanephosphonic acid esters is involved and gives, in some instances, only low yields of vinylphosphonic acid diesters, and the preparation starting from dichloroethanephosphonic acid esters is technically complicated, since, first of all, vinyl chloride is reacted with phosphorus trichloride in the presence of oxygen, and the resulting dichloroethanephosphonic acid esters are then further reacted with triethylamine and zinc dust in the presence of alcohols. It is further known to prepare dialkyl vinylphosphonates by thermolysing dialkyl 2-acetoxyethanephosphonates to split off acetic acid (cf. Nippon Kagaku Kaishi 10, 1991 (1972)). However, the yield of this method is only about 50%, and the reaction temperature is about 550° to 600° C., which is very high. The preparation of dialkyl vinylphosphonates from the corresponding 2-acetoxyethanephosphonic acid esters is also disclosed in German Offenlegungsschrift No. 3,120,438, according to which the dialkyl 2-acetoxyethanephosphonates are heated to 150° to 270° C. in the presence of acidic or basic catalysts, and the resulting reaction product is further reacted at 30° to 200° C. with orthoesters, for example with tetramethyl orthocarbonate, trimethyl orthoformate or trimethyl orthoacetate. In the examples of the German Offenlegungsschrift, where the yields of vinylphosphonic acid diesters are only about 70 to 85%, it also has to be taken into account that the vinylphosphonic acid half-esters formed first have to be further reacted with expensive orthoesters. Since the processes described above have partly considerable disadvantages it is desirable to have a process which will make dialkyl vinylphosphonates accessible in high yields and in an economical manner.

It has now been found that dialkyl vinylphosphonates can be prepared in a simple and economical manner by subjecting the new dialkyl 2-alkylcarbonateethanephosphonates to a catalyzed thermal cleavage.

The present invention accordingly provides new dialkyl 2-alkylcarbonatoethanephosphonates of the general formula (I)

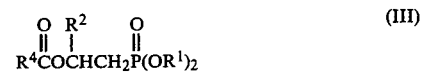

wherein
$R^1$ and $R^3$ are identical or different and each represents an alkyl group of 1 to 4 carbon atoms, and
$R^2$ denotes hydrogen, an alkyl group of 1 to 4 carbon atoms or unsubstituted phenyl, preferably hydrogen or methyl.

The following may be mentioned as examples of new dialkyl 2-alkylcarbonatoethanephosphonates which can be obtained according to the invention: dimethyl methylcarbonatoethanephosphonate, diethyl methylcarbonatoethanephosphonate, diethyl ethylcarbonatoethanephosphonate and dimethyl ethylcarbonatoethanephosphonate.

The dialkyl 2-alkylcarbonatoethanephosphonates of the formula (I) can be obtained in a simple manner by transesterifying dialkyl 2-carboxyethanephosphonates of the formula (III)

wherein
$R^1$ and $R^4$ are identical or different and each represents an alkyl group of 1 to 4 carbon atoms, and $R^4$ can also be hydrogen, and
$R^2$ has the abovementioned meaning, with dialkyl carbonates of the formula (IV)

wherein
$R^3$ has the abovementioned meaning, at about 110° to 160° C. in the presence of transesterification catalysts, and the carboxylic acid ester ($R^4COOR^3$) formed is distilled off.

Preferred compounds of the formulae (I), (III) and (IV) are those in which the alkyl groups have 1 or 2 carbon atoms. The following may be mentioned as alkyl radicals: methyl, ethyl, n-propyl, isopropyl, n-butyl, isobutyl and tert.-butyl, preferably methyl and ethyl.

Examples of possible dialkyl 2-carboxyethanephosphonates of the formula (III) are dimethyl, diethyl, diisopropyl or di-n-butyl 2-acetoxyethanephosphonate, 2-propoxyethanephosphonate or 2-butoxyethanephosphonate. The dimethyl and diethyl esters of acetoxyethanephosphonic acid are preferred.

The following may be mentioned as dialkyl carbonates of the formula (IV): dimethyl, diethyl, di-n-propyl, diisopropyl, di-n-butyl, diisobutyl and di-tert.-butyl carbonates, preferably dimethyl carbonate and diethyl carbonate.

The following may be mentioned as transesterification catalysts which are used in amounts of about 0.001 to 5% by weight, preferably 0.1 to 1% by weight, relative to the amount used of compound of the formula (III): $TiX_4$, $SnX_4$, $AlX_3$, $FeX_3$, $ZnX_2$, $ZrX_4$, $MoX_5$ and/or $VX_5$, wherein X represents halogen, such as chlorine or bromine, carboxyl, such as acetoxy, alkoxy, such as methoxy or ethoxy, or aryloxy, such as phenoxy.

The transesterification of dialkyl 2-carboxyethanephosphonates of the formula (III) is usually carried out at temperatures of about 100° to 220° C., preferably at 110° to 190° C., particularly preferably at 120° to 140° C.

In the transesterification, the carboxylic acid esters of the formula (IV) can be used, relative to the amount of dialkyl 2-carboxyethanephosphonate, in stoichiometric or higher or lower amounts. The carboxylic acid esters are preferably used in a molar ratio of 1:1 to 8:1 (carboxylic acid esters of the formula (IV):phosphonic acid esters of the formula (III)).

The transesterification can be carried out with or without an inert organic solvent. Examples of possible inert organic solvents are xylenes, halogenated hydrocarbons, such as o-dichlorobenzene, and ethers, such as anisole.

The alkyl carboxylate ($R^4COOR^3$) formed in the transesterification is advantageously distilled out of the reaction mixture.

The dialkyl 2-alkylcarbonatoethanephosphonates of the formula (I) can then be isolated from the remaining residue, and freed from the transesterification catalyst, by distillation under reduced pressure of about 0.001 to 100 mbar, preferably 0.01 to 20 mbar. Besides distillation, the transesterification catalyst can also be removed by means of a suitable extraction or adsorption process or by treatment with ion exchange materials, but it is not absolutely necessary to remove the transesterification catalyst for the subsequent cleavage of the dialkyl 2-alkylcarbonatoethanephosphonates of the formula (I).

The transesterification catalysts can be removed from the reaction mixture, for example, by extraction with water or with dilute aqueous acids, such as hydrochloric acid, sulphuric acid or acetic acid, or by an adsorption method, such as adsorption on active charcoal or kieselguhr. It is also possible, as mentioned above, to use ion exchange materials to remove the transesterification catalysts. Examples of such ion exchange materials are acid-activated bleaching earths or exchange resins based on sulphonated styrene/divinylbenzene copolymers.

To prepare vinylphosphonic acid diesters of the general formula (II)

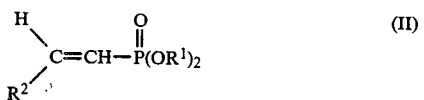

wherein
$R^1$ represents an alkyl group of 1 to 4, preferably 1 or 2, carbon atoms, and
$R^2$ represents hydrogen, an alkyl group of 1 to 4 carbon atoms or unsubstituted phenyl, preferably hydrogen or methyl,
the invention proposes heating dialkyl 2-alkylcarbonatoethanephosphonates of the general formula (I)

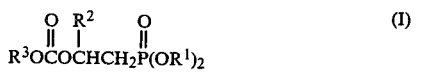

wherein
$R^1$ and $R^3$ are identical or different and each represents an alkyl group of 1 to 4, preferably 1 or 2, carbon atoms, and
$R^2$ denotes hydrogen, an alkyl group of 1 to 4 carbon atoms or unsubstituted phenyl, preferably hydrogen or methyl,
in the presence of catalysts.

In the process according to the invention, the dialkyl 2-alkylcarbonatoethanephosphonates of the formula (I) are heated to temperatures of about 160° to 250° C., preferably to 180° to 230° C. And it is advantageous to reduce the pressure to about 1 to 300 mbar, preferably 20 to 150 mbar.

Examples of catalysts possible for the thermal cleavage of the dialkyl 2-alkylcarbonatoethanephosphonates are the compounds of lithium, sodium, potassium, rubidium, caesium, magnesium, calcium, zinc, strontium, cadmium, barium, thallium and/or lead, preferably the compounds of alkali and/or alkaline earth metals. Generally, the hydroxides, alcoholates or the alkaline salts, such as the carbonates or the carboxylates, of said metals are used. The process according to the invention is preferably carried out with the carbonates, the carboxylates, the alcoholates and/or the hydroxides of sodium and/or of potassium, such as sodium hydroxide, sodium methanolate, potassium carbonate, sodium acetate and potassium isooctylate.

The catalysts are used in amounts of about 0.01 to 5% by weight, preferably 0.1 to 3% by weight, particularly preferably 0.5 to 2% by weight, relative to the amount of dialkyl 2-alkylcarbonatoethanephosphonate used.

The thermal cleavage of the alkylcarbonatoethanephosphonic acid esters can take the form of heating the alkylcarbonatoethanephosphonic acid esters for some time at about 180° to 200° C. under reduced pressure in the presence of, for example, potassium carbonate. The resulting cleavage products are condensed in a cooled receiving flask. To prevent any polymerization, polymerization inhibitors, such as hydroquinone or phenothiazine, can be added. The reaction product can subsequently be purified by distillation under reduced pressure of about 0.01 to 100, preferably 0.01 to 20 mbar. It is also possible to receive the cleavage products separately in a cooled receiving flask, in which way the vinylphosphonic acid ester desired is obtained directly in a highly pure form.

Dialkyl vinylphosphonates of the formula (II) are known intermediate products in the preparation of, inter alia, flame retardants (cf. German Offenlegungsschrift No. 2,452,369). They also serve as comonomers for the preparation of synthetic polymers (cf. German Auslegeschrift No. 1,052,118 and J. Chem. Soc. 1956, 4607).

EXAMPLE 1

Diethyl ethylcarbonatoethanephosphonate 224 g (1 mole) of diethyl 2-acetoxyethanephosphonate, 472 g (4 moles) of diethyl carbonate and 5 ml of tetrabutyl titanate are heated in a 1.2 m packed column at an internal temperature of 127° to 135° C. for 5 hours. 83 g of ethyl acetate are distilled off at the top. After removal of excess diethyl carbonate under reduced pressure of 10 to 60 mbar, 249 g of crude product are left behind. Distillation under 0.03 mbar gives 204 g of the title compound in a pure form; boiling point 89° to 92° C./0.03, $n_D^{20}=1.4309$ (yield 80%, relative to diethyl 2-acetoxyethanephosphonate).

EXAMPLE 2

Diethyl vinylphosphonate (a) 85 g (0.334 mole) of diethyl ethylcarbonatoethanephosphonate from Example 1 are admixed with 200 mg of potassium carbonate, and the mixture is heated at 190° C. for 2.5 hours under reduced pressure, which was initially 300 mbar and which was reduced, towards the end of the reaction, to 20 mbar. The cleavage products are condensed in a cooled receiving flask at 0° C., and the $CO_2$ is absorbed in a liquid nitrogen trap. Distillation of the condensate under reduced pressure gave: 47 g of diethyl vinylphosphonate (boiling point 80° to 82° C./9), 10 g of uncleaved diethyl ethylcarbonatoethanephosphonate and 14 g of ethanol. The yield was 97%, relative to reacted diethyl ethylcarbonatoethanephosphonate.

(b) 44 g (0.173 mole) of diethyl ethylcarbonatoethanephosphonate, prepared as in Example 1 but not distilled, were admixed with 400 mg of potassium carbonate, and the mixture was reacted as described in Example 2(a). Distillation under reduced pressure gave: 14.4 g of diethyl vinylphosphonate and 15 g of diethyl ethylcarbonatoethanephosphonate. The yield was 77%, relative to reacted ethylcarbonatoethanephosphonic acid diester.

What is claimed is:

1. Dialkyl 2-alkylcarbonatoethanephosphonate of the formula

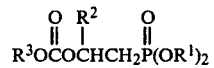

wherein
R$^1$ and R$^3$ are identical or different and each represents an alkyl group of 1 to 4 carbon atoms, and
R$^2$ denotes hydrogen, an alkyl group of 1 to 4 carbon atoms or unsubstituted phenyl.

* * * * *